(12) United States Patent
Hosemann et al.

(10) Patent No.: US 11,226,422 B2
(45) Date of Patent: Jan. 18, 2022

(54) X-RAY DETECTOR AND X-RAY DEVICE WITH X-RAY DETECTOR

(71) Applicant: Siemens Healthcare GmbH, Erlangen (DE)

(72) Inventors: Michael Hosemann, Erlangen (DE); Thorsten Ergler, Erlangen (DE); Jan Wrege, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/916,686

(22) Filed: Jun. 30, 2020

(65) Prior Publication Data

US 2021/0011181 A1 Jan. 14, 2021

(30) Foreign Application Priority Data

Jul. 8, 2019 (EP) .................................... 19184975

(51) Int. Cl.
*G01T 1/24* (2006.01)
*A61B 6/00* (2006.01)
*G01T 1/17* (2006.01)
*H04N 5/32* (2006.01)

(52) U.S. Cl.
CPC ............ *G01T 1/247* (2013.01); *A61B 6/4241* (2013.01); *G01T 1/17* (2013.01); *H04N 5/32* (2013.01)

(58) Field of Classification Search
CPC ......... G01T 1/247; G01T 1/17; A61B 6/4241; H04N 5/32
See application file for complete search history.

(56) References Cited

U.S. PATENT DOCUMENTS

| | | | | |
|---|---|---|---|---|
| 5,671,266 A | * | 9/1997 | Linhart | A61B 6/4482 378/175 |
| 7,075,090 B2 | * | 7/2006 | Endo | G01N 23/04 250/370.11 |
| 2005/0169426 A1 | * | 8/2005 | Groh | A61B 6/4266 378/98.8 |
| 2006/0124856 A1 | | 6/2006 | Heismann | |
| 2007/0076937 A1 | * | 4/2007 | Spahn | G06T 7/136 382/132 |
| 2010/0260313 A1 | * | 10/2010 | Kudo | H04N 5/378 378/19 |
| 2015/0102227 A1 | * | 4/2015 | Nyg rd | G01T 1/247 250/370.09 |
| 2015/0253437 A1 | | 9/2015 | Goderer et al. | |
| 2017/0038480 A1 | * | 2/2017 | Groepl | G01T 1/247 |
| 2017/0090048 A1 | * | 3/2017 | Groepl | H03M 1/662 |
| 2019/0011578 A1 | | 1/2019 | Ergler et al. | |
| 2019/0154852 A1 | * | 5/2019 | McCroskey | G01T 1/2985 |

FOREIGN PATENT DOCUMENTS

| | | |
|---|---|---|
| DE | 102004057533 A1 | 6/2006 |
| DE | 102012202200 B3 | 4/2013 |
| DE | 102014204042 A1 | 9/2015 |
| JP | 2009018109 A | 1/2009 |

* cited by examiner

*Primary Examiner* — Blake C Riddick
(74) *Attorney, Agent, or Firm* — Harness, Dickey & Pierce, P.L.C.

(57) ABSTRACT

An x-ray detector includes a sensor slice for directly converting x-ray radiation and a downstream read-out chip. Further, in at least one embodiment, a first amplifier stage is interconnected between the sensor slice and read-out chip.

19 Claims, 3 Drawing Sheets

X-RAY DETECTOR AND X-RAY DEVICE WITH X-RAY DETECTOR

PRIORITY STATEMENT

The present application hereby claims priority under 35 U.S.C. § 119 to European patent application number EP 19184975.1 filed Jul. 8, 2019, the entire contents of which are hereby incorporated herein by reference.

FIELD

Embodiments of the invention generally relate to an x-ray detector having a sensor slice and a downstream read-out chip. Furthermore, embodiments of the invention generally relate to an x-ray device with such an x-ray detector.

BACKGROUND

In image-generating x-ray devices, what are known as directly converting x-ray detectors are used increasingly, such as are described for instance in DE 10 2012 202 200 B3. These x-ray detectors are typically embodied as what are known as photon-counting x-ray detectors and as essential components have a sensor slice and a read-out chip.

In this regard the read-out chip is currently linked directly to the sensor slice so that the very small analog signal pulses, which are generated by x-ray quanta in the sensor material of the sensor slice, reach the read-out chip in as pure and low-noise a manner as possible and can be processed or measured there. Here an amplifier stage is connected in the read-out chip on the input side, said amplifier stage amplifying these signal pulses and thus rendering them robust against interferences for the further processing in the read-out chip.

In order now to realize a large sensor surface with one such x-ray detector, a number of subunits, known as sensor boards, are typically tiled closely against one another. In this way it is essential to the imaging that the set-up of the x-ray detector or rather the sensor surface takes place in as gap-free a manner as possible. In order to enable this, through-connections, known as TSVs, are typically introduced into the read-out chip, since then the subunits can also be lined up directly on four sides without any problem. The production of read-out chips with through-connections is very complicated, however, and as a result also cost-intensive.

SUMMARY

If, by contrast, other approaches are chosen for connecting the read-out chip, in which the read-out chip is not linked directly to the sensor slice, the inventors have discovered that there is the problem that longer lines or even different line lengths for different pixels significantly influence the response behavior of the read-out chip. This can go so far that the image quality is influenced problematically.

At least one embodiment of the invention specifies an advantageously configured x-ray detector and an advantageously configured x-ray device with a corresponding x-ray detector.

Embodiment of the invention are directed to an x-ray detector and an x-ray device. The related claims contain in part advantageous and in part per se inventive developments of this invention. The advantages cited in relation to the x-ray detector and preferred embodiments can also be applied, mutatis mutandis, to the x-ray device.

At least one embodiment of the inventive x-ray detector is here embodied expediently for use in an x-ray device, for instance a computed tomography system, and has a sensor slice and a downstream read-out chip, wherein the read-out chip is preferably configured as what is known as an ASIC read-out chip (ASIC: application-specific integrated circuit).

At least one embodiment is directed to an x-ray detector, comprising:
a sensor slice to directly convert x-ray radiation; and
a downstream read-out chip; and
a first amplifier stage, interconnected between the sensor slice and the read-out chip.

At least one embodiment is directed to an x-ray device, comprising:
an x-ray radiation source; and
the x-ray detector of an embodiment.

BRIEF DESCRIPTION OF THE DRAWINGS

Example embodiments of the invention are shown in more detail below on the basis of a schematic drawing. In the drawings.

Parts corresponding to one another are labeled with the same reference characters in all the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially de signed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In this regard the x-ray detector and/or the sensor slice is typically assembled from a number of subunits or modules, which are typically configured to be essentially identical. If the x-ray detector is assembled from modules, each x-ray detector module typically has a corresponding sensor slice and at least one corresponding downstream read-out chip.

Irrespective of whether or not there is now a modular set-up, in accordance with at least one embodiment of the invention a first amplifier stage is interconnected between the sensor slice and the read-out chip, wherein this first amplifier stage is expediently likewise embodied as a type of slice, in other words a type of functional slice. Here the first amplifier stage is typically positioned directly or immediately on the sensor slice and is in particular connected in an electrically conductive manner directly or immediately herewith, for instance by way of solder connections.

Here the first amplifier stage is preferably connected to the sensor slice by way of very short and in particular identical electrically conductive connections or bridgings, in other words in particular solder connections, so that these electrically conductive connections have no significant parasitic capacitances and/or resistances. By way of the first amplifier stage, during operation of the x-ray detector the sensor signals or sensor pulses from the sensor slice are then amplified by the first amplifier stage, even before parasitic capacitances and/or resistances become effective and as a result the amplified sensor signals are then insensitive to the effects of parasitic capacitances and/or resistances in the electrically conductive connection toward the read-out chip.

The amplified sensor signals are therefore then led to the read-out chip almost unaffected by the further line lengths and/or the further line capacitances and are further processed there. As a result, new possibilities result with respect to the embodiment of the electrically conductive connections to the read-out chip. This enables in particular to become more independent of the input capacitances toward the inputs of the read-out chip.

In this regard the basic idea can also be seen as that of shifting, on the basis of an x-ray detector with a read-out chip according to the prior art, the amplifier function or at least one part of the amplifier function of the read-out chip out of the read-out chip into a further or separate component plane. In this way this new, separate component plane is positioned close to the sensor slice. This enables a wide spatial separation of the sensor slice and read-out chip by taking the problem into account, that the sensor layer delivers very small analog sensor signals in the pA region, but an accurate detection/evaluation of the sensor signals in the read-out chip should still take place.

Furthermore, the x-ray detector is embodied as what is known as a directly converting x-ray detector or photon-counting x-ray detector and accordingly CdTe, CdZnTe, CdZnTeSe, CdTeSe, CdNnTe, InP, TIBr$_2$, or HgI$_2$ is a main component of the sensor slice, for instance. The sensor slice or converter slice is used here in a manner known per se to directly convert x-ray radiation into electrical signals, in other words sensor signals, wherein the sensor signals are typically present as current pulses.

Moreover, the x-ray detector or each x-ray detector module expediently has a plurality of pixels, wherein a volume element of the sensor slice typically belongs to each pixel and a signal processing unit linked in an electrically conductive manner thereto. Part of such a signal processing unit is here generally an amplifier circuit of the first amplifier stage and a read-out circuit in the read-out chip. In this regard the sensor signals of the various pixels generated in the sensor slice are typically amplified, processed and evaluated at least at the start independently of one another and accordingly the first amplifier stage then typically has a separate amplifier circuit for each pixel and the read-out chip typically has a signal input per pixel. A pixel by pixel amplification therefore takes place in particular by way of the first amplifier stage.

In this regard the amplifier circuits of the first amplifier stage are typically realized via simple transistor circuits, which are produced in most cases by the use of a CMOS technology. Irrespective of this, depending on the application, a current amplification is realized with an amplification factor via a corresponding amplifier circuit, the value of which lies in the region of approx. 2 to approx. 100 and in particular in the region of approx. 2 to approx. 50. As an alternative or in addition, a current-to-voltage conversion is realized in the first amplifier stage, wherein in this case the current values are preferably converted into voltage values with a factor in the region of approx. 1 mV/nA to approx. 100 nV/nA and in particular in the region of approx. 1 mV/nA to approx. 50 mV/nA.

In any case, an active amplification is preferably performed via the first amplifier stage and accordingly the first amplifier stage is supplied with electrical power during operation. I.e. the first amplifier stage has a supply input for electrical power, via which during operation of the first amplifier stage electrical power is supplied for active amplification of sensor signals.

According to a preferred embodiment of the x-ray detector, the read-out chip moreover has a second amplifier stage which is integrated into the read-out chip and is thus part of the read-out chip. The second amplifier stage here typically has an amplifier circuit per pixel, wherein one such amplifier circuit is typically arranged immediately downstream of an input. In this regard the amplifier circuits of the second amplifier stage are preferably kept simpler than with a read-out chip according to the prior art, since amplification already takes place during operation by the first amplifier stage.

The amplification realized with an amplifier circuit of the second amplifier stage typically complies here with the amplification realized by the first amplifier stage and/or subsequently whether a current-to-voltage conversion is or will be realized via the first amplifier stage. In this regard the second amplifier stage is preferably configured so that voltage signals are present at the latest at the outputs of the second amplifier stage, namely in particular voltage signals, the typical pulse heights of which lie in the region of approx. 10 mV to approx. 150 mV depending on the energy of the x-ray quanta. Depending on the design, in other words depending on the production process selected and its preferred operating voltage and the required linearity (avoiding the saturation as a result of what is known as pile-up), these values still possibly deviate by a factor up to approx. 5. The typically very large fluctuation range is frequently influenced here by many different factors.

Since the amplification realized with an amplifier circuit of the second amplifier stage preferably complies with the embodiment of the first amplifier stage, in some instances even a larger or even a targeted amplification is omitted by way of the second amplifier stage. In one such case, a filtering of the signal amplified via the first amplifier stage takes place via an amplifier circuit of the second amplifier stage, this filtering is also referred as pulse shaping, and/or a current-to-voltage conversion. Typical amplification factors are then only present in the region of approx. 1 to approx. 10.

Furthermore, the read-out chip typically has a filter circuit per pixel, which is typically arranged downstream of the amplifier circuit of the second amplifier stage. Moreover, the read-out chip typically has one counter circuit per pixel, which then typically closes the pixel-by-pixel processing of the sensor signals.

Furthermore one embodiment of the x-ray detector is advantageous, in which what is known as an interposer is interconnected between the sensor slice and the read-out chip. The interposer, also known as rewiring unit or reconnection unit, is used here to connect two units in an electrically conductive manner to one another, each of which has a number of electrical contacts or terminals, in which the electrical contacts or terminals are arranged differently, however, so that simple direction connections, for instance solder connections, cannot be embodied.

If one such interposer is provided, this is further preferably arranged downstream of the first amplifier stage and the first amplifier stage is then accordingly preferably interconnected between the sensor layer and interposer.

According to one embodiment variant, the first amplifier stage is further manufactured by way of a method based on TFT technology (thin-film transistor). This technology makes it possible to manufacture transistors on glass, and is already used in large-scale production, for instance to manufacture displays.

In particular, if the first amplifier stage is manufactured on the basis of a TFT technology, it is moreover advantageous if the interposer is configured as a glass interposer, wherein the first amplifier stage is then further preferably manufactured on the glass interposer by way of a method based on TFT technology. Here technologies for manufacturing through-connections and/or rewiring layers in glass are already available and pure interposers made from glass (without amplifier stage) are already known. These technologies are now used in the case of an embodiment variant of the x-ray detector, in order to manufacture an interposer from glass, which additionally has the first amplifier stage.

Alternatively, instead of an interposer made from glass, an interposer based on a semiconductor material, for instance silicon, is used and in this case the x-ray detector then has one such interposer based on a semiconductor material. An interposer of this type is then typically assembled from a number of slices or layers and the first amplifier stage is preferably embodied by way of at least one of these layers.

In an advantageous development a redistribution layer (RDL) is arranged downstream of the layer of the interposer forming the first amplifier stage and all redistribution layers of the interposer are typically arranged downstream of the layer forming the first amplifier stage.

The interposer then includes, for instance, a number of layers, wherein a layer made from silicon is embodied as a base material and wherein the first amplifier stage is integrated into this layer. To this end, CMOS technology can be used, for instance, by which amplifier circuits are integrated individually or in groups of several amplifiers into layers of the interposer. To this end these layers typically have cutouts. Moreover, one such interposer typically has at least one redistribution layer, in which conductor paths made from copper run, for instance.

Furthermore, one embodiment variant of the x-ray detector is advantageous, in which the first amplifier stage is realized on a film. In this regard the first amplifier stage is preferably printed onto the film and accordingly the electrical and/or electronic modules of the amplifier stage are then applied to the film via printing technology.

One such film is then expediently laminated onto the sensor slice, or, if available, onto an interposer, in other words for instance glued. The fastening is preferably carried out by way of a type of adhesion, wherein a conductive adhesive is preferably used for electrical contacts.

One embodiment variant of the x-ray detector is further considered to be advantageous, in which the first amplifier stage is applied to the sensor layer. In this case the first amplifier stage is preferably realized by a semiconductor slice or semiconductor layer, which is applied to the sensor slice via epitaxy, in other words either directly or indirectly by way of an intermediate layer or intermediate slice.

A silicon slice or silicon layer is therefore deposited on the sensor slice via epitaxy and the first amplifier stage is then implanted into this silicon slice. In this regard, depending on the application case, an intermediate layer comprising silicon dioxide is firstly deposited on the sensor slice and the silicon slice is then embodied.

An embodiment variant of the x-ray detector is moreover expedient, in which a conductor board is interconnected between the first amplifier stage and the read-out chip. Depending on the embodiment variant the conductor board is embodied here as a rigid conductor board, as a flexible conductor board or as a partially rigid and partially flexible conductor board.

An x-ray detector 2 described subsequently is embodied as a directly converting x-ray detector 2 and is shown schematically in FIG. 1 in a first embodiment variant.

Figure 2:
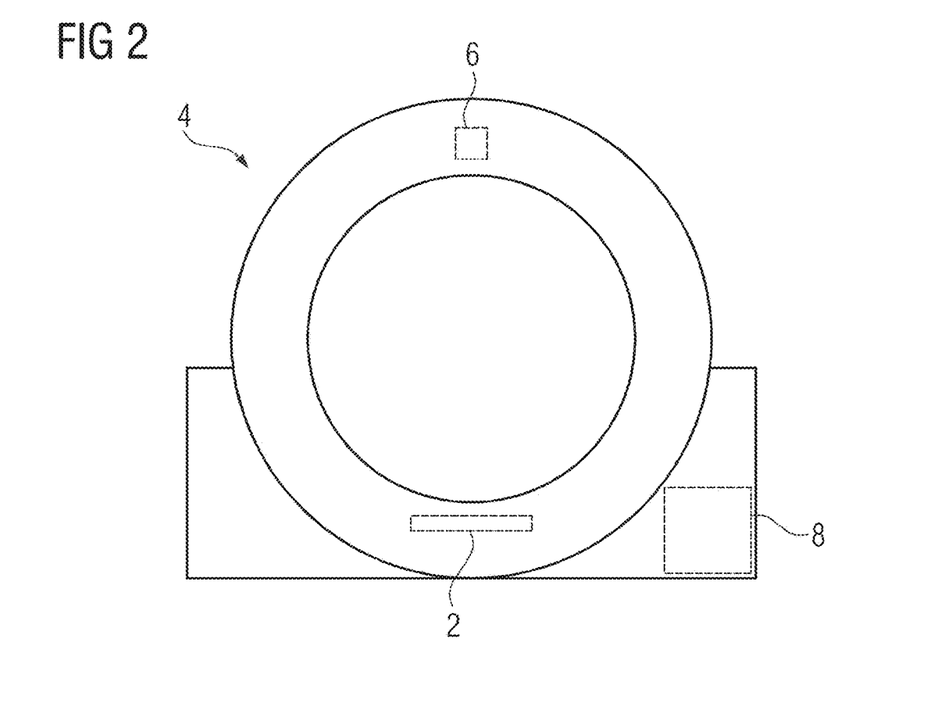
FIG. 2 shows a semitransparent view of an x-ray device with the x-ray detector.

In the example embodiment, the x-ray detector 2 is here an integral part of an x-ray device 4, which is embodied by way of example as a computed tomography system and is outlined in FIG. 2. In the x-ray device 4, the x-ray detector 2 is extended by an x-ray radiation source 6. Moreover, the x-ray device 4 has a control unit 8.

The x-ray detector 2, as already shown, is configured as a directly converting x-ray detector 2, and as essential components has a converter slice or sensor slice 10, a first amplifier stage 12, an interposer 14 and an ASIC read-out chip 16.

Moreover, the x-ray detector 2 has a plurality of pixels 18 or forms a plurality of pixels 18, wherein a volume element 20 of the sensor slice 10 and a signal processing unit 22 belongs to each pixel 18. By way of example one such pixel 18 is reproduced in FIG. 3 in the form of a simplified block diagram.

Figure 3:
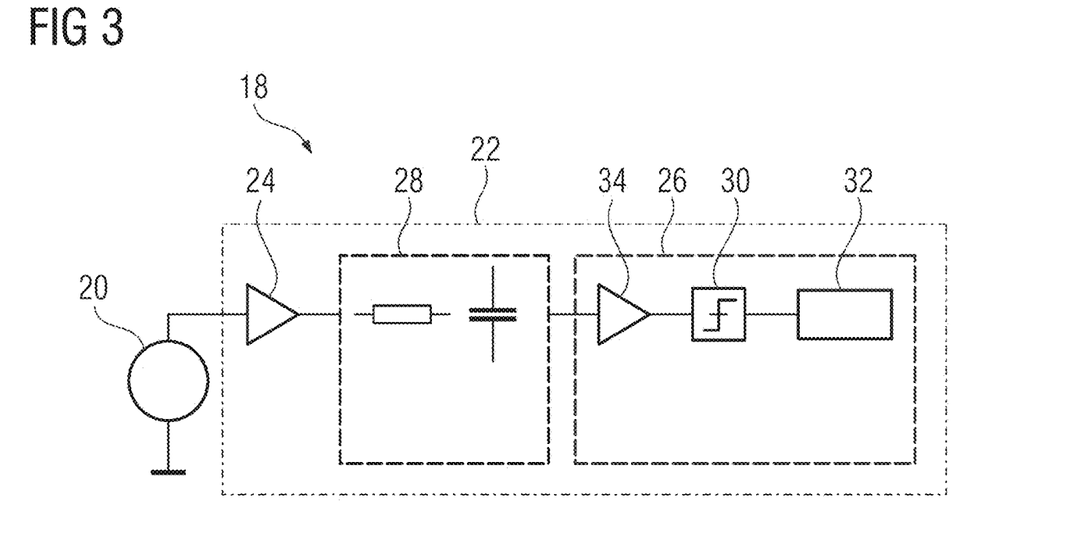
FIG. 3 shows a circuit diagram of a pixel of the x-ray detector.

In the example embodiment each signal processing unit 22 is in turn formed by a first amplifier circuit 24, which is part of the first amplifier stage 12, and a read-out circuit 26, which is part of the ASIC read-out chip 16, wherein the first amplifier circuit 24 is connected via an interposer connection 28, which is part of the interposer 14, to the read-out circuit 26. Each pixel 18 therefore has a volume element 20 and a signal processing unit 22 with a first amplifier circuit 24, with an interposer connection 28 and with a read-out circuit 26. In this regard one such interposer connection 28 typically has a characteristic parasitic capacitance and a characteristic parasitic resistance.

As a result of this embodiment, a sensor signal generated in a volume element 20 of a pixel 18 is then firstly amplified during operation of the x-ray detector 2 in the first amplifier circuit 24 of the corresponding pixel 18 linked to the volume element 20. The amplified sensor signal is then forwarded to the ASIC read-out chip 16 via the interposer connection 28 of this pixel 18 and is further processed there in the read-out circuit 26 of the pixel 18.

In the example embodiment the signal processing units 22 of the pixel 18 operate independently of one another and in each pixel 18 the striking x-ray quanta are counted, wherein the read-out circuit 26 in the ASIC read-out chip 16 for this purpose typically has a comparator 30 and a counter unit 32. Moreover, in the example embodiment each read-out circuit 26 has a second amplifier circuit 34 and all second amplifier circuits 34 of the ASIC read-out chip 16 together form a second amplifier stage.

Figure 1:
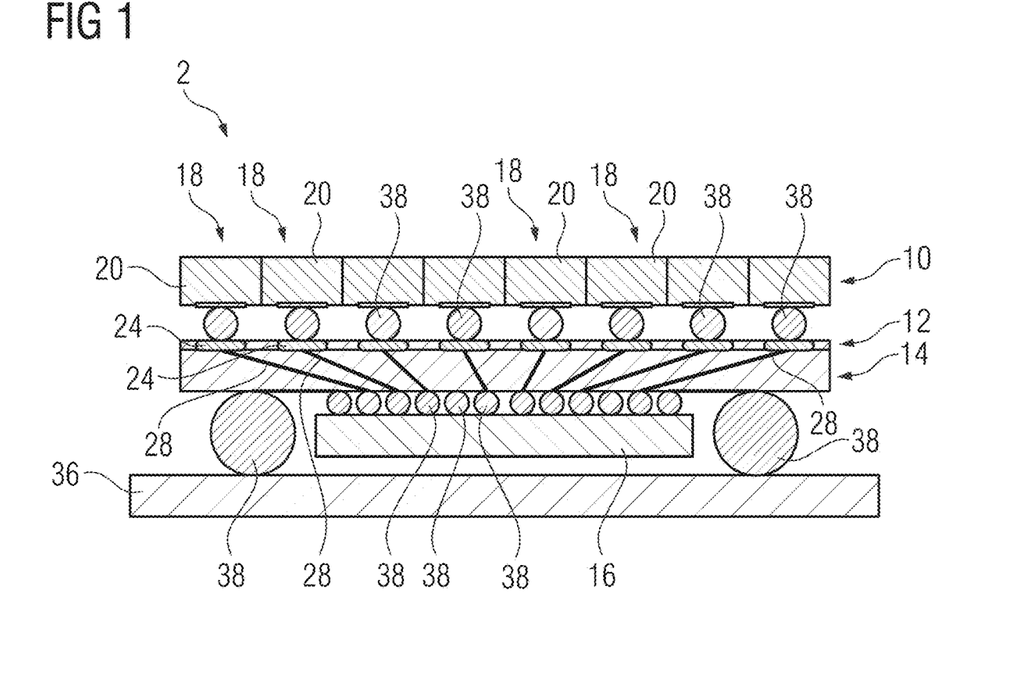
FIG. 1 shows a first embodiment of an x-ray detector in a partially cross-sectional representation.

In FIG. 1 a first embodiment variant of the x-ray detector 2 is now reproduced schematically in a partially sectional representation. The representation shows that the interposer 14 is interconnected between the sensor layer 10 and ASIC read-out chip 16 and that the ASIC read-out chip 16 is finally connected in an electrically conductive manner to a conductor board 36 or linked to the conductor board 36.

Furthermore, the first amplifier stage 12 is interconnected between the sensor layer 10 and interposer 14, wherein in the example embodiment simple solder connections 38 are embodied between the sensor layer 10 and the first amplifier stage 12. Here a volume element 20 is connected in an electrically conductive manner to a first amplifier circuit 24 of the first amplifier stage 12 by way of one such solder connection 38.

In this regard, depending on the embodiment variant, the first amplifier stage 12 is realized for instance on a film, not shown explicitly, in other words for instance printed on a film, and the film is laminated onto the sensor layer 10 or the interposer 14, for instance.

Alternatively, the first amplifier stage 12 is manufactured by way of a method based on a TFT technology and realized on the interposer 14, which is then preferably embodied as a glass interposer.

Figure 4:
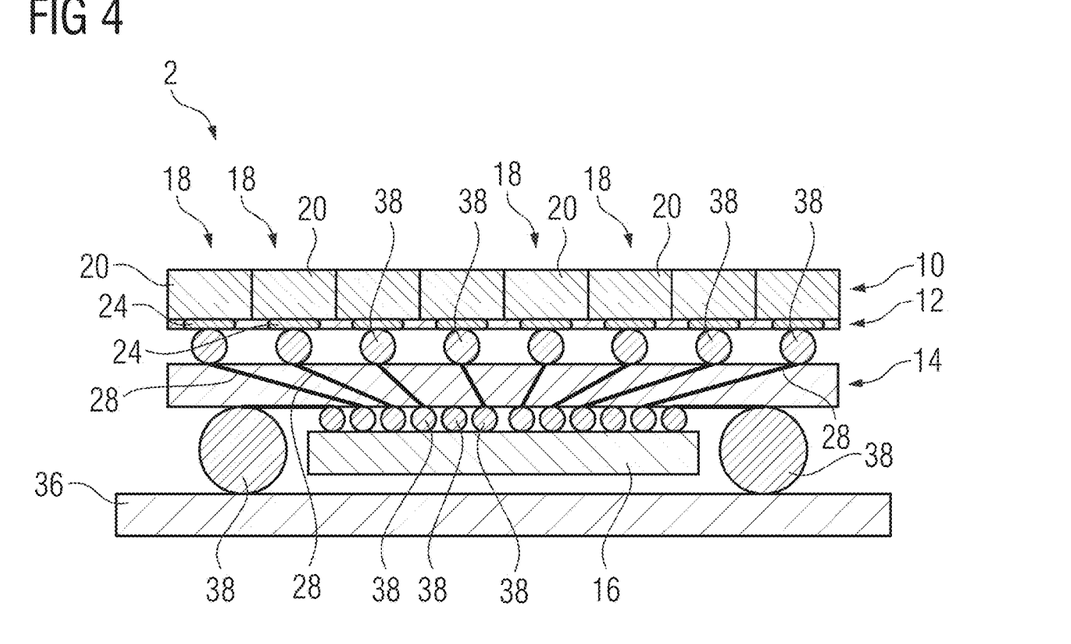
FIG. 4 shows a partial cross-sectional representation of a second embodiment of the x-ray detector.

A second embodiment variant of the x-ray detector 2 is shown in FIG. 4, at least in simplified form. Here the first amplifier stage 12 is embodied directly on the sensor slice 10, wherein to this end in the example embodiment a silicon slice or silicon layer is applied to the sensor slice 10 via epitaxy and wherein the semiconductor circuits, not shown in detail, and forming the first amplifier stage 12 are integrated into this silicon slice or are realized in the silicon slice. Here silicon only represents a suitable material example. In particular, if gallium arsenide is used as a sensor material of the sensor slice 10, it is likewise favorable if an epitaxy layer with semiconductor circuits and/or amplifiers in the gallium arsenide technology is realized.

Figure 5:
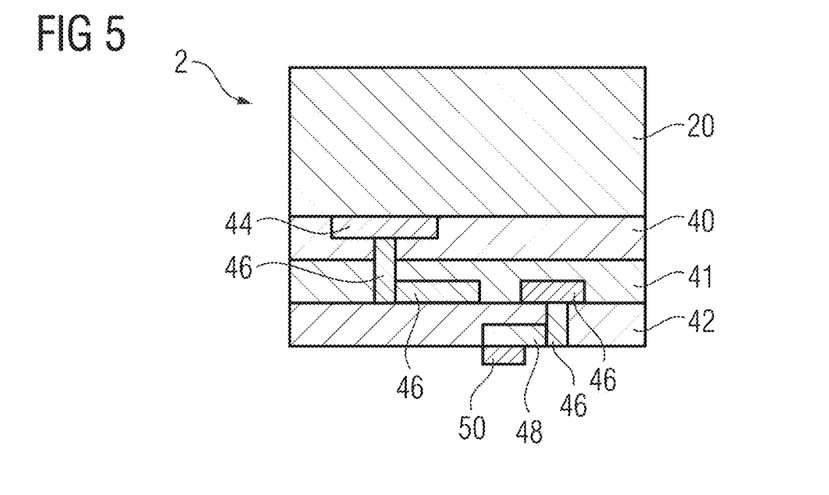
FIG. 5 shows a partial cross-sectional representation of a third embodiment of the x-ray detector and FIG. 6 shows a partially cross-sectional representation of a fourth embodiment of the x-ray detector.

A further embodiment variant of the x-ray detector 2 is indicated in FIG. 5. A number of layers 40, 41, 42, namely a first layer 40, an intermediate layer 41 and a redistribution layer 42, are attached to the sensor layer 10, wherein the first amplifier stage 12 is realized in the intermediate layer 41. Since in the example embodiment according to FIG. 5 the reconnection is at least carried out across all three layers 40, 41, 42 shown, in principle in this example embodiment all three layers 40, 41, 42 form the interposer 14, wherein in this interposer 14 the first amplifier stage 12 is embodied in the intermediate layer 41.

A basic design in the region of a pixel 18 is shown here in FIG. 5. A metal contact 44 firstly connects to the volume element 20 of the pixel. Here the first layer 40 made from silicon is embedded in each metal contact 44. Two further layers made from silicon connect to this first layer 40, wherein circuit structures 46, which form the first amplifier circuit 24 of this pixel 18, are embodied in the intermediate layer 41 via doping circuit structures 46. The third layer 42, which is used as a redistribution layer 42, has conductor paths 48 made from copper 48, by which an output 50 of the interposer which is guided outward is positioned, so that this can be connected in an electrically conductive manner directly to an input on the ASIC read-out chip 16 by way of a solder connection 38 and is also connected in the x-ray detector 2.

The third embodiment of the x-ray detector 2 according to FIG. 5 is also adjusted in some instances so that the intermediate layer 41 is replaced by a number of comparable intermediate layers/intermediate slices. The reason for this is then typically that additional wirings for instance for power supply and/or for distributing signals are also still realized for the first amplifier circuit 24. Such wirings are then frequently realized in a number of slices.

Figure 6:
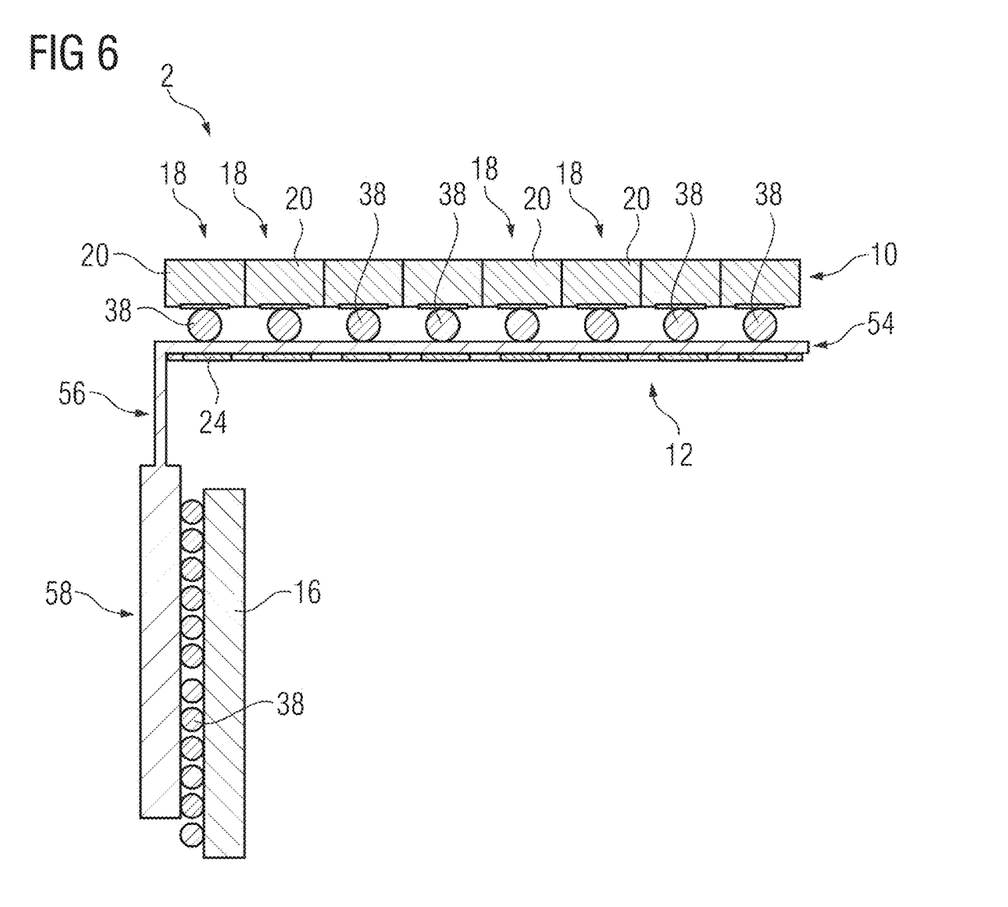

A fourth example embodiment of the x-ray detector 2 is reproduced schematically in FIG. 6. Here the ASIC read-out chip 16 is linked to the first amplifier stage 12 by way of a partially flexible, partially rigid conductor board 52, wherein this conductor board 52 functions as a type of interposer 14. The first amplifier stage 12 itself is connected here in an electrically conductive manner to the sensor slice 10 by way of through connections and solder connections 38, not shown in more detail here.

Moreover, the first amplifier stage 12 is realized on a thin, rigid first part 54 of the conductor board 52. It is manufactured in a simple and cost-effective circuit process. That first part 54 of the conductor board 52 is connected to an in turn rigid third part 58 by way of a flexible, second part 56, to which third part the ASIC read-out chip 16 is linked. The ASIC read-out chip 16 is manufactured in a more complicated and expensive process and realized on a significantly smaller surface.

The invention is not restricted to the example embodiment described above. Rather, other variants of the invention can also be derived herefrom by the person skilled in the art, without departing from the subject matter of the invention. In particular all the individual features described in relation to the example embodiment can also be combined differently with one another, without departing from the subject matter of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray detector, comprising:
   a sensor slice to directly convert x-ray radiation; and
   a downstream read-out chip;
   a first amplifier stage, connected between the sensor slice and the downstream read-out chip; and
   an interposer, connected between the sensor slice and downstream read-out chip, the interposer including a number of layers and the first amplifier stage being embodied by at least one layer of the number of layers.

2. The x-ray detector of claim 1, wherein the downstream read-out chip includes a second amplifier stage.

3. The x-ray detector of claim 1, wherein the first amplifier stage is connected between the sensor slice and the interposer.

4. The x-ray detector of claim 3, wherein a glass interposer is connected as the interposer between the sensor slice and downstream read-out chip and wherein the first amplifier stage is manufactured on the glass interposer via a thin film technology (TFT) methodology.

5. The x-ray detector of claim 1, wherein the first amplifier stage is a thin film transistor (TFT).

6. The x-ray detector of claim 1, wherein the interposer is a glass interposer, connected between the sensor slice and downstream read-out chip and wherein the first amplifier stage is manufactured on the glass interposer via thin film transistor (TFT) technology methodology.

7. The x-ray detector of claim 1, wherein the at least one layer embodying the first amplifier stage is arranged upstream of a redistribution layer.

8. The x-ray detector of claim 1, wherein the first amplifier stage is realized on a film.

9. The x-ray detector of claim 8, wherein the first amplifier stage is printed on the film.

10. The x-ray detector of claim 8, wherein the film is laminated onto the sensor slice or the interposer.

11. The x-ray detector of claim 1, wherein the first amplifier stage is attached to the sensor slice.

12. The x-ray detector of claim 11, wherein a conductor board is connected between the first amplifier stage and the downstream read-out chip.

13. The x-ray detector of claim 1, wherein the first amplifier stage is realized by a semiconductor slice, applied to the sensor slice via epitaxy.

14. An x-ray device, comprising:
    an x-ray radiation source; and
    the x-ray detector of claim 1.

15. The x-ray detector of claim 1, wherein the first amplifier is configured to amplify signals from the sensor slice to provide the detector with amplified signals insensitive to effects of at least one of parasitic capacitance and parasitic resistance.

16. An x-ray detector, comprising:
    a sensor slice to directly convert x-ray radiation;
    a downstream read-out chip;
    an interposer, including a number of layers, connected between the sensor slice and the downstream read-out chip; and
    a first amplifier stage, connected between the sensor slice and the interposer, embodied by at least one layer of the number of layers.

17. The x-ray detector of claim 16, wherein the at least one layer embodying the first amplifier stage is arranged upstream of a redistribution layer.

18. An x-ray device, comprising:
    an x-ray radiation source; and
    the x-ray detector of claim 16.

19. The x-ray detector of claim 16, wherein the first amplifier is configured to amplify signals from the sensor slice to provide the detector with amplified signals insensitive to effects of at least one of parasitic capacitance and parasitic resistance.

* * * * *